Aug. 23, 19[illegible] C. F. ZAIGER Plant Pat. 2,6[illegible]3
PEACH TREE
Filed July 26, 19[illegible]
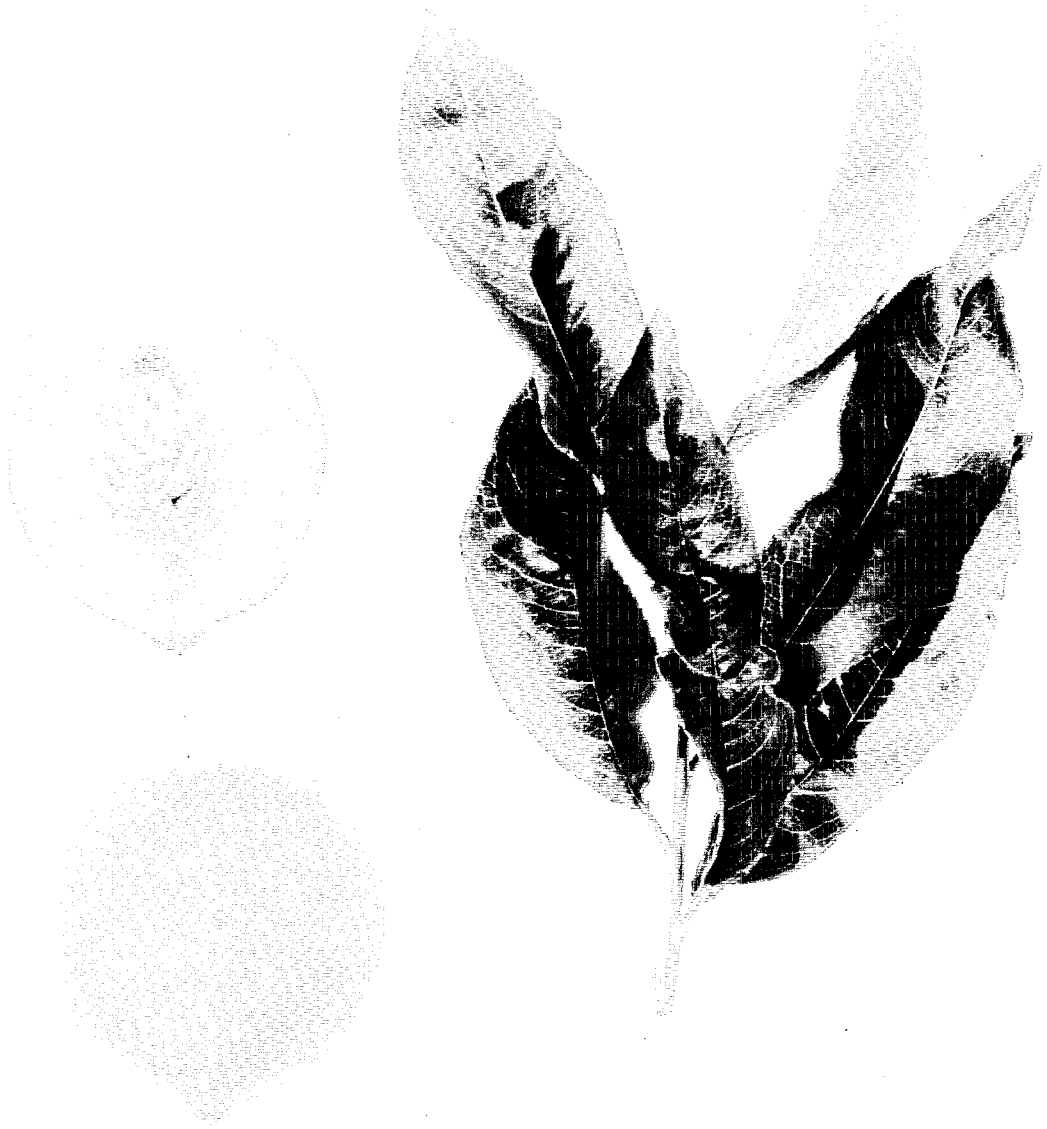
INVENTOR
C. Floyd Zaiger United States Patent Office Plant Pat. 2,663

Patented August 23, 1966

2,663

PEACH TREE

Chris Floyd Zaiger, 537 Rosemore Ave., Modesto, Calif.

Filed July 26, 1965, Ser. No. 475,027

1 Claim. (Cl. Plt.—43)

The present discovery relates to a new variety of peach tree which originated as a bud sport of Springtime (United States Plant Patent No. 1,268).

The sport was discovered by me in my orchard in May 1961, and has been reproduced by me in my nursery at 537 Rosemore, Modesto, county of Stanislaus, State of California, by budding. The asexual reproduction of this new variety shows the subsequently described characteristics to be consistent and well established.

The new variety is characterized as to novelty when compared with the Springtime by ripening two to four days earlier, having yellow flesh, greater firmness, and having larger fruit, the fruit being of darker and brighter red color at maturity. The fruit being freestone when fully ripe but even then is frequently subject to some minor adherence of the flesh to the pit.

It will be recognized that the present peach fulfills a demand for a commercially desirable peach having yellow flesh, greater firmness, larger size, higher color, and ripening two to four days earlier than Springtime.

In the accompanying photographs are shown characteristic fruit and leaves of my new variety peach.

Referring now more specifically to the pomological details of this new and distinct variety of peach tree, the following is an outline description thereof. All major color plate identifications being by reference to Maerz and Paul "A Dictionary of Color."

Tree:

*Size.*—Medium to large.
*Vigor.*—Vigorous.
*Growth.*—Medium upright.
*Density.*—Medium dense.
*Shape.*—Normally pruned to vase form.
*Productivity.*—Productive.
*Bearing.*—Regular bearer.

Trunk:

*Size.*—Medium stocky.
*Surface.*—Shaggy.

Branches:

*Size.*—Medium stocky.
*Surface.*—Medium shaggy.
*Color.*—Brown to grayish (reddish) brown.
*Lenticels.*—Medium quantity.

Leaves:

*Size.*—Medium. Mature length — 5" to 6½". Width—1" to 2". Average—1⅝".
*Form.*—Lanceolate; acutely pointed.
*Texture.*—Smooth.
*Petiole.*—Medium length; medium thickness.
*Glands.*—Average number—four. Opposite; medium size, globose; yellowish-green. On lower part of leaf and upper part of petiole.
*Margin.*—Crenate.
*Color.*—Top side—medium green (23–L–4). Under side—lighter green (22–I–5). Heavy midrib on under side yellowish-green (19–K–1).

Flower buds:

*Size.*—Medium.
*Length.*—Short.
*Form.*—Plump; free.
*Pubescence.*—Pubescent.

Flowers:

*Blooming period.*—Date of first bloom—March 2, 1964. Date of full bloom—March 12, 1964. Size—Medium. Color—Pink. Pollen—Present.

Fruit:

*Maturity when described.*—Hard ripe.
*Date of first picking.*—May 21, 1964.
*Date of last picking.*—May 28, 1964.
*Size.*—Large. Diameter axially — 2¼" to 3". Suture plane—2½" to 3".
*Form.*—Globose to slightly flattened at stem end in larger sizes, some oblong in smaller sizes.
*Suture.*—Shallow and nearly disappears at maturity.
*Ventral surface.*—Rounded and only very slightly lipped.
*Apex.*—Varied from slightly retuse to small sharply pointed pistil point.
*Cavity.*—Rounded. Average depth, ⅜"; average breadth, 1".
*Base.*—Retuse.

Flesh: Relatively firm.

*Color.*—Light yellow near stem end (9–L–5) grading to darker yellow at the apex (9–L–8).
*Amygdalin.*—Undetected.
*Juice.*—Abundant and rich.
*Texture.*—Firm and crisp.
*Fibers.*—Few and tender.
*Ripens.*—Rather evenly.
*Flavor.*—Mildly acid to sweet, but is primarily sweet.
*Aroma.*—Fragrant.
*Eating quality.*—Excellent.

Skin:

*Thickness.*—Medium.
*Texture.*—Medium tender. Tenacious to flesh when firm ripe. Free when soft ripe.
*Tendency to crack.*—None.
*Down.*—Moderate; medium length.
*Color.*—Bright yellow under color (9–K–5) shading to (9–K–7), to as dark as (11–G–9). Red blush covering most of the surface of the peach, grading from a light red (3–L–1) to dark red (6–L–5).

Stone: Free but tight when not fully ripe, parts from flesh but frequently retains thin filaments of flesh along ridges near base.

*Size.*—Medium, average length 1½ inches, average width 1", average thickness ⅝ inch.
*Fibres.*—Few on grooved side.
*Form.*—Obovate, tip acuminate.
*Base.*—Long tapering.
*Hilum.*—Oval and shallow.
*Apex.*—Acuminate.
*Sides.*—Substantially symmetrical.
*Surface.*—Irregularly furrowed toward apex, pitted toward base.
*Color.*—Light tan.
*Tendency to split.*—Slight but noticeable.

Use: Excellent for dessert, culinary uses, canning, freezing, and shipment, when compared with other varieties ripening therewith in the same area.

Keeping quality: Excellent.

Shipping quality: Good.

The subject peach tree and its fruit may vary in minor particulars due to climatic, soil, and other enviromental variations but has been described as observed under cultivation in the San Joaquin Valley of California.

Having thus described my discovery, I claim:

A new and distinct variety of peach tree, substantially as illustrated and described bearing large, firm, freestone fruit having yellow flesh and being characterized as to novelty when compared with the Springtime by ripening 2 to 4 days earlier, having larger fruit, the fruit being yellow fleshed and having a brighter red blush color.

No references cited.

ABRAHAM G. STONE, *Primary Examiner.*

R. E. BAGWILL, *Assistant Examiner.*